United States Patent
Landry et al.

(10) Patent No.: US 9,028,433 B2
(45) Date of Patent: May 12, 2015

(54) LIMB STRENGTH MEASUREMENT DEVICE

(71) Applicant: University of New Brunswick, Fredericton (CA)

(72) Inventors: John Stephen Landry, Fredericton (CA); Andrew Mark Sexton, Douglas (CA); Glen Hughes, Fredericton (CA); Chris A. McGibbon, Fredericton (CA)

(73) Assignee: University of New Brunswick, Fredericton, New Brunswick (CA)

( * ) Notice: Subject to any disclaimer, the term of this patent is extended or adjusted under 35 U.S.C. 154(b) by 248 days.

(21) Appl. No.: 13/800,009

(22) Filed: Mar. 13, 2013

(65) Prior Publication Data

US 2013/0289448 A1    Oct. 31, 2013

Related U.S. Application Data

(60) Provisional application No. 61/638,690, filed on Apr. 26, 2012.

(51) Int. Cl.
*A61B 5/00* (2006.01)
*A61B 5/11* (2006.01)

(52) U.S. Cl.
CPC .............. *A61B 5/11* (2013.01); *A61B 5/1124* (2013.01); *A61B 5/6823* (2013.01)

(58) Field of Classification Search
CPC ....... A61B 5/11; A61B 5/1124; A61B 5/6823
USPC ........ 600/587, 595; 482/131–137; 73/379.01, 73/379.02
See application file for complete search history.

(56) References Cited

U.S. PATENT DOCUMENTS

| | | |
|---|---|---|
| 4,179,923 A | 12/1979 | Dodt |
| 4,702,108 A | 10/1987 | Amundsen et al. |
| 4,882,677 A | 11/1989 | Curran |
| 4,909,262 A | 3/1990 | Halpern et al. |
| 5,052,375 A | 10/1991 | Stark et al. |
| 5,131,408 A | 7/1992 | Smith |
| 5,662,591 A | 9/1997 | Peindl et al. |
| 5,954,621 A | 9/1999 | Joutras et al. |

(Continued)

FOREIGN PATENT DOCUMENTS

WO    2008080233 A1    7/2008

OTHER PUBLICATIONS

Abdulrahman, S.A. et al., "Normal isometric and isokinetic peak torques of hamstring and quadriceps muscles in young adult saudi males", Neuroscience vol. 9 (3): 165-170, 2004.

(Continued)

*Primary Examiner* — Max Hindenburg
(74) *Attorney, Agent, or Firm* — Hill & Schumacher; Lynn C. Schumacher

(57) ABSTRACT

Wearable devices, and methods of use thereof, are provided for the measurement of isometric limb strength. In some embodiments, the device includes pivotally connected members and associated contact pads for contacting portions of a limb, where the members may be locked in position to perform isometric flexion or extension force measurements of the limb about a joint. A load cell or other force measurement sensor integrated with the device measures the force applied to one of the contact pads, either directly or indirectly. In some embodiments, the device can be reconfigured for the measurement of isometric strength for both flexion and extension.

25 Claims, 16 Drawing Sheets

(56) References Cited

U.S. PATENT DOCUMENTS

| | | | |
|---|---|---|---|
| 5,976,063 | A | 11/1999 | Joutras et al. |
| 5,980,435 | A | 11/1999 | Joutras et al. |
| 6,227,047 | B1 | 5/2001 | Livingston |
| 6,296,595 | B1 | 10/2001 | Stark et al. |
| 6,872,187 | B1 | 3/2005 | Stark et al. |
| 7,493,812 | B2 | 2/2009 | Andres et al. |
| 7,615,025 | B2 | 11/2009 | Nathanson |
| 7,748,271 | B2 | 7/2010 | Kadota |
| 8,028,576 | B2 | 10/2011 | Oster |
| 2005/0107726 | A1 | 5/2005 | Oyen et al. |
| 2008/0041153 | A1 | 2/2008 | Tokita |
| 2008/0202233 | A1 | 8/2008 | Lan et al. |
| 2010/0050765 | A1 | 3/2010 | Kadota et al. |
| 2010/0240495 | A1 | 9/2010 | Law et al. |

OTHER PUBLICATIONS

Cortez, P. J. O. et al., "A device to assess the upper limb isometric muscle strength", Cornell University Library, arXiv.0905.2439, pp. 1-4, May 18, 2009.

Cortez P. J. O. et al. "A new device to measure isometric strength in upper limbs: comparison between dominant and non-dominant limbs", Clinics, 66(2), pp. 351-354, Feb. 2011.

Finucane, S.D. et al., "Reliability of isometric muscle testing of knee flexor and extensor muscles in patients with connective tissue disease", Physical Therapy, vol. 68, pp. 338-343, 1988.

Ford-Smith, C. et al., "Reliability of Stationary Dynamometer Muscle Strength Testing in Community-Dwelling Older Adults", Arch. Phys. Med. Rehabil. 82, 1128-1132, 2001.

Gagnon, D., et al., "Reliability and Validity of Static Knee Strength Measurements Obtained With a Chair-Fixed Dynamometer in Subjects With Hip or Knee Arthroplasty", Arch. Phys. Med. Rehabil. 86, 2005-2008, 2005.

Kollock J., et al., "The Reliability of Portable Fixed Dynamometry During Hip and Knee Strength Assessments", Athletic Training 45, 349-356, 2010.

Nadler, S. et al., "Portable Dynamometer Anchoring Station for Measuring Strength of the Hip Extensors and Abductors", Arch. Phys. Med. Rehabil. 81, 1072-1076, 2000.

Scott, D., Arch. Phys. Med. Rehabil., "The Intra- and Interrater Reliability of Hip Muscle Strength Assessments Using a Handheld Versus a Portable Dynamometer Anchoring Station", 85, 598-603, 2004.

Corrected International Search Report—PCT/CA2013/050189 dated Jun. 21, 2013.

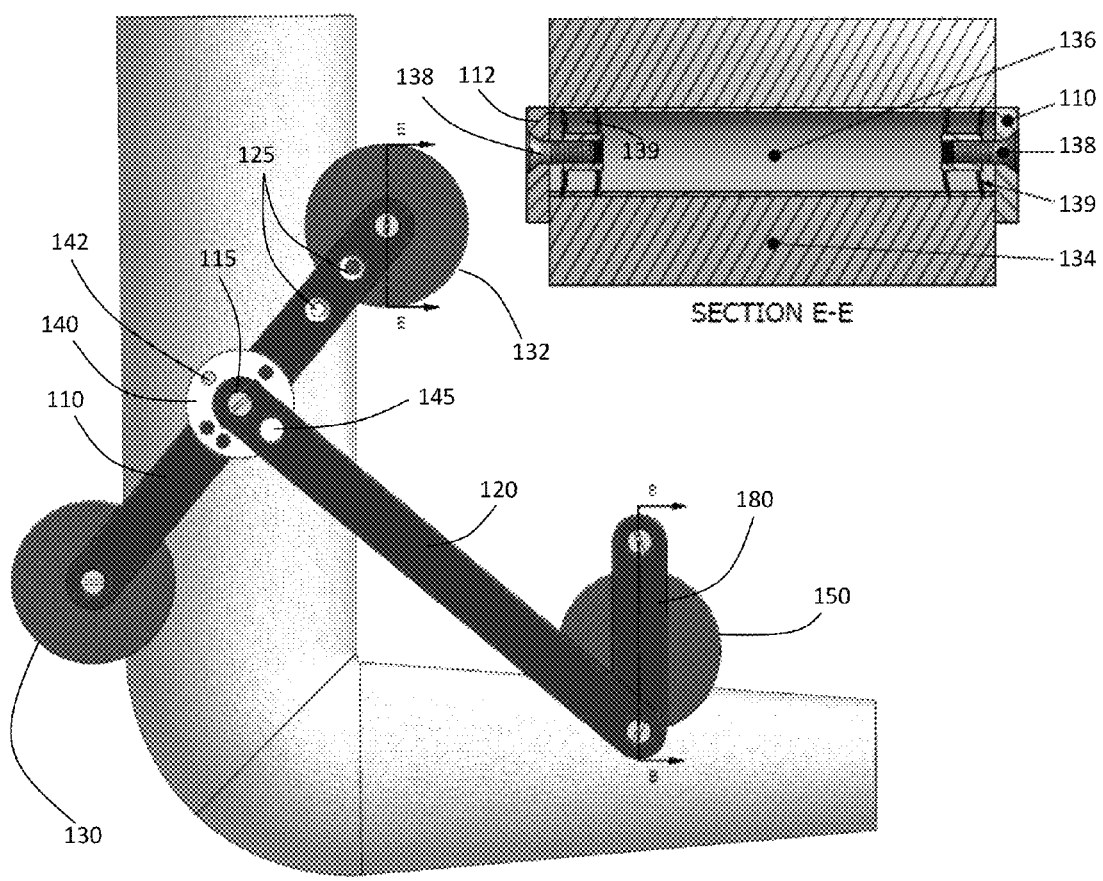

LIMB STRENGTH MEASUREMENT DEVICE

CROSS-REFERENCE TO RELATED APPLICATION

This application claims priority to U.S. Provisional Application No. 61/638,690, titled "LIMB STRENGTH MEASUREMENT DEVICE" and filed on Apr. 26, 2012, the entire contents of which is incorporated herein by reference.

BACKGROUND

The present disclosure relates to methods and devices for exercise and physical therapy. More particularly, the present disclosure relates to methods and devices for strength measurement.

Muscle strength measurement is an important component of physical therapy and rehabilitation and sport science in general. Rehabilitation outcomes for many diseases, disorders and injuries, ranging from stroke in older populations to athletic injuries in younger populations requires assessment of muscle strength in a clinical environment. Research in rehabilitation and sport science often use muscle strength as a primary outcome, and furthermore requires measurement of "maximal voluntary isometric contraction" to normalize muscle electromyography assessments.

There are currently two choices for obtaining quantitative measurement of muscle strength. Isometric dynamometry systems can accurately and reliably measure both isokinetic and isometric muscle strength, but very few clinical facilities have access to such equipment due to its cost of purchase and maintenance as well as its space requirements. Furthermore, typical systems that objectively quantify limb flexion and extension strength are large apparatuses attached to the wall or floor which are not easily portable.

Hand-held dynamometry systems are considerably cheaper and require far less resources to maintain, but usually require a trained user to hold the device steady while the subject, who must also remain steady, applies a force. Testing of major joints (like the knee and elbow) with such a device can thus be difficult to perform, mostly in terms of the tester stabilizing themselves against the patient's ability to generate force.

SUMMARY

Wearable devices, and methods of use thereof, are provided for the measurement of isometric limb strength. In some embodiments, the device includes pivotally connected members and associated contact pads for contacting portions of a limb, where the members may be locked in position to perform isometric flexion or extension force measurements of the limb about a joint. A load cell or other force measurement sensor integrated with the device measures the force applied to one of the contact pads, either directly or indirectly. In some embodiments, the device can be reconfigured for the measurement of isometric strength for both flexion and extension.

Accordingly, in a first aspect, there is provided a limb strength measurement device for measuring strength of a limb under isometric flexion or extension, the limb having a first portion and a second portion pivotable about a joint, the device comprising: a first pair of longitudinal members provided in a spaced relationship, wherein a gap between the first pair of longitudinal members is suitable for insertion of the limb therethrough, a first contact pad supported between the first pair of longitudinal members near a first end thereof; a second contact pad supported between the first pair of longitudinal members near a second end thereof; a second pair of longitudinal members provided in a spaced relationship, wherein the second pair of longitudinal members are pivotally connected to the first pair of longitudinal members near a first end of the second pair of longitudinal members, and wherein a gap between the second pair of longitudinal members is suitable for insertion of the limb therethrough; a third contact pad coupled to the second pair of longitudinal members near a second end thereof, a locking mechanism for locking an angular orientation of the second pair of longitudinal members relative to the first pair of longitudinal members, such that when the device is worn, the first contact pad and the second contact pad contact opposing sides of the first portion of the limb, and the third contact pad contacts the second portion of the limb, thereby securing the device relative to the limb; and a force measurement device configured to measure a force applied to the third contact pad by the second portion of the limb.

In another aspect, there is provided a limb strength measurement device for measuring strength of a limb under flexion or extension, the limb having a first portion and a second portion pivotable about a joint, the device comprising: a first longitudinal member; a second longitudinal member pivotally connected to the first longitudinal member near a first end of the second longitudinal member; a first contact pad extending laterally from the first longitudinal member near a first end thereof; a second contact pad extending laterally from the first longitudinal member near a second end thereof; a third contact pad coupled to the second longitudinal member near a second end thereof, a locking mechanism for locking an angular orientation of the second longitudinal member relative to the first longitudinal member, such that when the device is worn, the first contact pad and the second contact pad contact opposing sides of the first portion of the limb, and the third contact pad contacts the second portion of the limb, thereby securing the device relative to the limb; and a force measurement device configured to measure a force applied to the third contact pad by the second portion of the limb.

In another aspect, there is provided a limb strength measurement device for measuring strength of a limb under isometric flexion or extension, the limb having a first portion and a second portion pivotable about a joint, the device comprising: a first pair of longitudinal members provided in a spaced relationship, wherein a gap between the first pair of longitudinal members is suitable for insertion of the limb therethrough, a first contact pad supported between the first pair of longitudinal members near a first end thereof; a second contact pad supported between the first pair of longitudinal members near a second end thereof; a second pair of longitudinal members provided in a spaced relationship, wherein the second pair of longitudinal members are pivotally connected to the first pair of longitudinal members at a pivot location, and wherein a gap between the second pair of longitudinal members is suitable for insertion of the limb therethrough; a third contact pad supported between the second pair of longitudinal members near a first end thereof, wherein the first end of the second pair of longitudinal members is distal from the pivot location, and a force measurement device restricting pivotal motion of the second pair of longitudinal members beyond a pre-selected angle when the first contact pad and the second contact pad contact opposing sides of the first portion of the limb and the third contact pad contacts the second portion of the limb; wherein the force measurement device is configured to indirectly measure a force applied to the third contact pad by the second portion of the limb.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which.

DETAILED DESCRIPTION

Figure 1A:
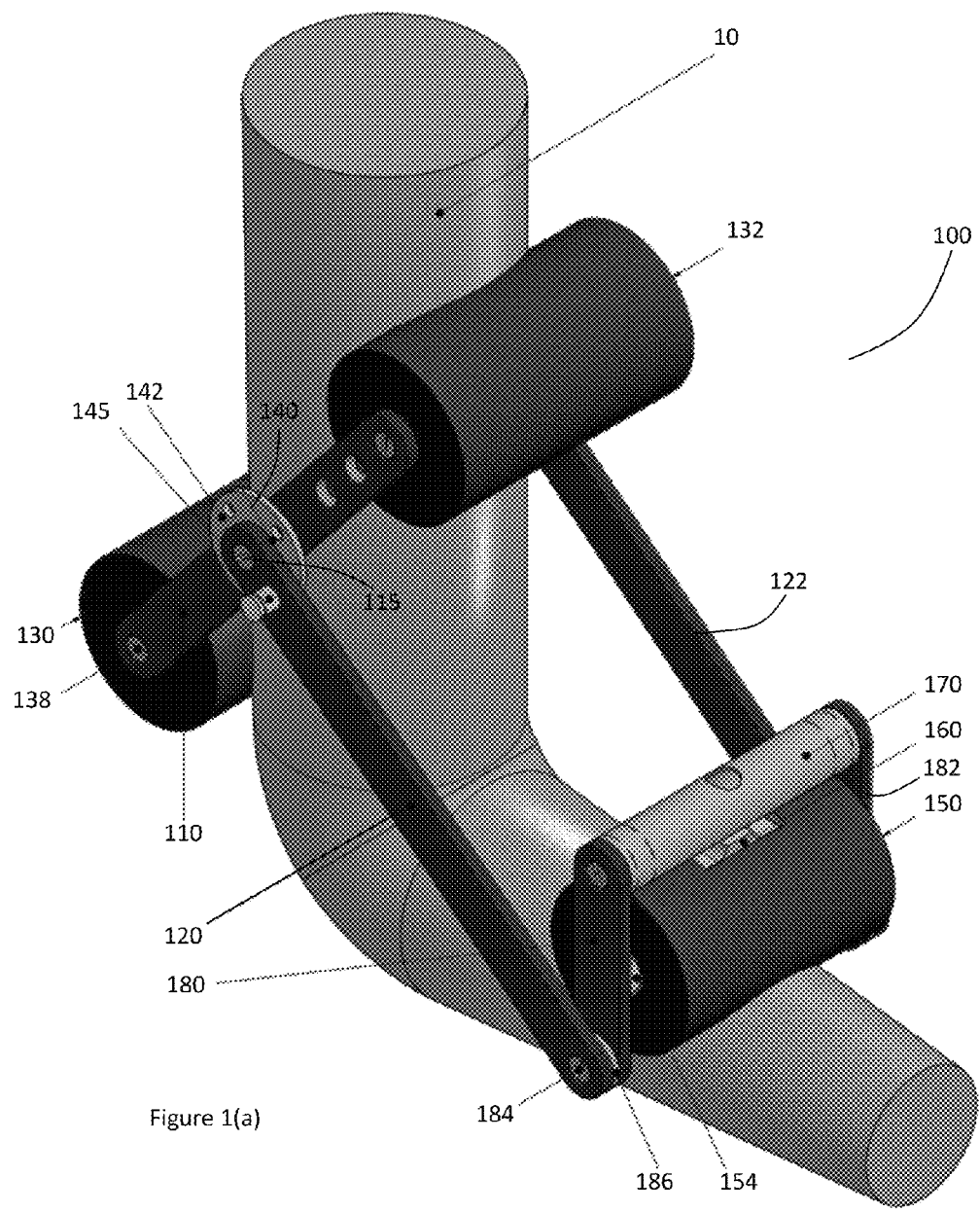
FIG. 1 shows views of a limb strength measurement device, showing (a) an isometric view, (b) a lateral view, (c) a cross sectional view of the second contact pad, and (d) a cross-sectional view of the third contact pad having an integrated load cell.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure. It should be understood that the order of the steps of the methods disclosed herein is immaterial so long as the methods remain operable. Moreover, two or more steps may be conducted simultaneously or in a different order than recited herein unless otherwise specified.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately", when used in conjunction with ranges of dimensions of particles, compositions of mixtures or other physical properties or characteristics, are meant to cover slight variations that may exist in the upper and lower limits of the ranges of dimensions so as to not exclude embodiments where on average most of the dimensions are satisfied but where statistically dimensions may exist outside this region. It is not the intention to exclude embodiments such as these from the present disclosure.

Embodiments of the present disclosure provide devices, and methods of use thereof, for the measurement of isometric limb strength using a wearable system of sensors and mechanical constraints. The device is self-contained, self-stabilizing, and easily donned and doffed from the arm or leg. In some embodiments, the limb strength measurement device can be reconfigured for the measurement of isometric strength of both flexor and extensor muscles of the joint.

FIGS. 1(a)-(d) show one embodiment of a wearable isometric limb strength measurement device 100 that is configured for the measurement of isometric flexion and/or extension force of a limb. In the present example embodiment, device 100 is shown positioned on arm 10, where the device has a size suitable for the measurement of isometric flexion or extension strength of an elbow joint.

Device 100 includes first pair of longitudinal members 110,112 and second pair of longitudinal members 120, 122, that are each provided in a spaced relationship, with a spacing suitable for the insertion of a limb (arm 10). First pair of members 110, 112 support first contact pad 130 and second pad 132, which are configured to contact opposing sides of a first segment of a wearer's limb when worn. FIG. 1 only shows one member 110 of first pair of longitudinal members 110, 112 with the other member 112 of the pair hidden by arm 10. The other member 112 is visible, for example, in FIGS. 3 and 4.

FIG. 1(c) illustrates an example internal structure of first 130 and second 132 contact pads. Second contact pad 132 is shown in the Figure as cylindrical in shape, with an annular form core 134 surrounding a tubular cross member 136 and an optional outer covering (not shown). Cross member 136 is connected to first pair of longitudinal members 110 and 112 through screws 138, which are received in tube connecting nuts 139. Although cross member 136 is shown as a hollow tubular member, it may alternatively be a solid member having lateral threaded holes for receiving screws 138 or other suitable fastening elements.

FIG. 1(b) also illustrates an example embodiment in which first pair of longitudinal members 110 and 112 (not shown in the Figure) include additional mounting features, such as holes 125, for selectively positioning second contact pad 132 in multiple positions relative to first contact pad 130, in order to adjust the spacing between first and second contact pads 130 and 132 (as further illustrated at 190 in FIG. 3(b)). Such an embodiment allows a single device to accommodate a variety of limb sizes.

First pair of members 110, 112 are pivotally connected to second pair of members 120, 122, through a suitable pivot element such as a pin or screw, and may be locked together at a fixed angle, as further described below. As shown in FIG. 1(b), member 110 is pivotally connected to member 120 via screw 115.

The relative angular orientation of first pair of longitudinal members 110, 112 and second pair of longitudinal members 120, 122 may be fixed by a locking mechanism such as a locking plate and locking pin (which may be spring-loaded for convenient engagement and disengagement). FIGS. 1 (a) and (b) provide an example embodiment in which locking plate 140, having a plurality of locking holes 142, is affixed to first member 110. A similar locking mechanism exists between members 112 and 122, as shown in FIG. 2(a) where locking plate 148 is shown as connected to member 122.

Although the Figures show a locking mechanism involving a series of holes in a locking plate, other locking mechanisms may alternatively be employed for fixing the angular orientation of the first and second pairs of members. For example, the locking plate may have an azimuthally oriented slot for receiving a bolt passing through a hole in member 110. The slot could include a series of outer projections into which a spring-biased bolt or other suitable detent mechanism could be positioned, with each outer projection defining a pre-selected angular orientation.

Figure 2A:
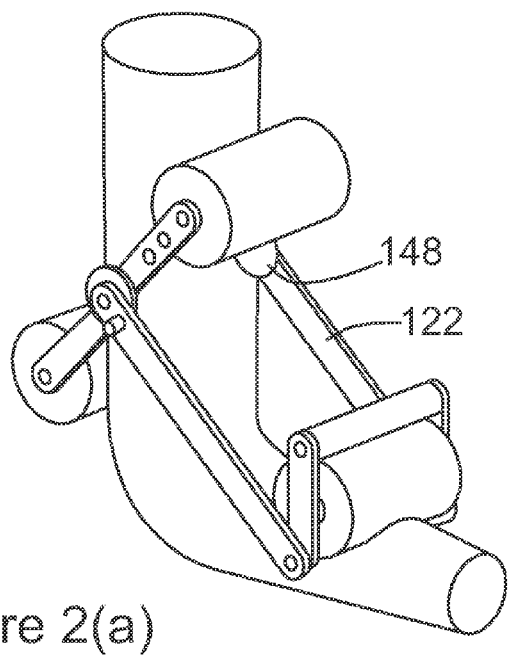
FIG. 2 shows different embodiments of the limb strength measurement device, in which (a) shows a device sized for use in measuring elbow joint strength, and (b) shows a device sized for use in measuring knee joint strength.

In FIG. 1(a), third contact pad 150 is supported near a distal end of second pair of longitudinal members 120, 122, and is configured to contact the second portion of limb 10 when worn, such that the device is self-stabilizing when locked in position. Under flexion of the elbow joint, an isometric force is applied to third contact pad 150. This force is detected by load cell 160, as further described below.

Figure 1D:
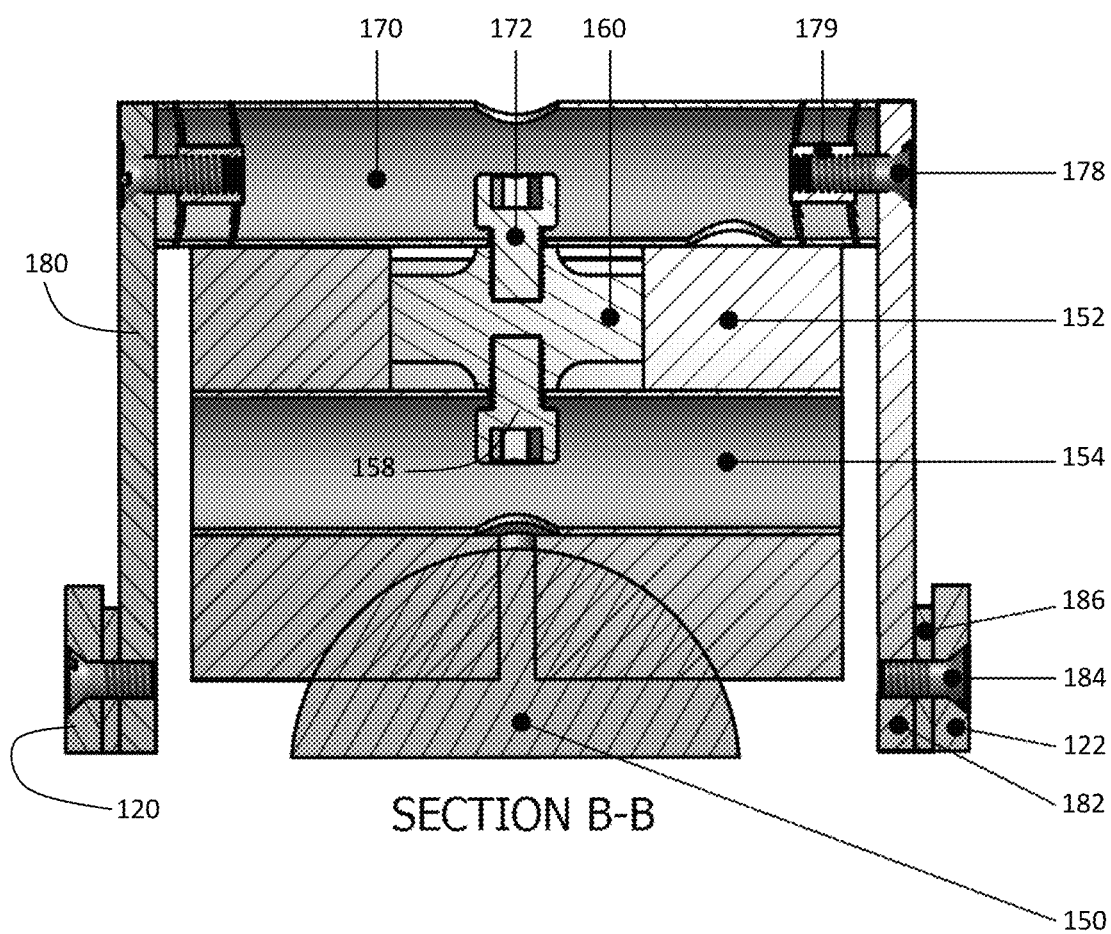

Referring now to FIG. 1(d), a cross-sectional diagram is shown that illustrates the transduction of an applied flexion force and the measurement of the force by integrated load cell 160. As shown in the Figure, third contact pad 150 is shown in the Figure as cylindrical in shape, with an annular form core 152 surrounding a tubular member 154 and an optional outer covering (not shown). Tubular member 154 is connected to a first side of load cell 160 via screw 158, such that load cell 160 is recessed in an outer radial portion of third contact pad 150.

Load cell 160 is connected, on a second side thereof, to second tubular cross member 170, through screw 172. Second cross member 170 is connected to third pair of members 180, 182 through screws 178, which are received in tube connecting nuts 179. Third pair of members 180, 182 are pivotally connected to distal ends of second pair of longitudinal members 120, 122 through a pivotal connection element such as a pin or screw (e.g. screws 184 and washers 186).

Accordingly, it is apparent in FIG. 1(a) that third contact pad 150 is indirectly coupled to second pair of longitudinal members 120, 122 near their distal end, where the coupling is provided through third pair of members 180, 182 (member 182 is shown in FIG. 1(d)), second cross member 170, and load cell 160. When strength measurement device 100 is positioned on the arm of the wearer and locked in position for the measurement of the isometric flexion force as shown, the application of an isometric flexion force to third contact pad results in the compression of the contact pads, and the transfer of the isometric flexion force to load cell 160, where the force is measured. The locking of the orientation of first pair of longitudinal members 110, 112 and second pair of longitudinal members 120, 122 ensures that the orientation of the device is fixed during the application of the force, thereby allowing for the measurement of an isometric force.

As shown in FIG. 1(b), third pair of members 180, 182 are connected to second cross member 170 such that their longitudinal axis is parallel to the axis of load cell 160. The pivotal connection of third pair of members 180, 182 to second pair of longitudinal members 120, 122 allows the rotation of third contact pad 150 such that the direction of applied force is substantially parallel to the axis of load cell 160. Due to the presence of the third pair of members 180,182, pivot point 184 remains positioned approximately at the midpoint of the forearm. From this central point, the load cell swings from above the forearm for flexion to under the forearm for extension (as further described below), contacting the forearm in either configuration at approximately the same longitudinal distance from the elbow joint.

Furthermore, the third pair of members, 180, 182, allow for a pivoting point at the connection with 120, 122 such that when the force of the limb is applied to the third pad, 150, the bars 180, 182 will move to essentially be in alignment with the direction of the applied force. This helps to make a more absolute measure of the applied force when varying sizes and shapes and tapers of human limbs are applied. Without this self aligning aspect, the measured force would differ from the true applied force by a factor of the cosine of the angle difference between the direction of the applied force and axis of the load cell. The pivot point helps to minimize this angle to 0, i.e. cosine (0)=1.0.

The force measured by the load cell may be, in some example embodiments, directly read from a display or gauge provided in or on the device, or indirectly obtained from an external display and/or processing unit. In one example, the load cell requires an input analog voltage and produces an output analog voltage that is externally digitized by an Analog to Digital Convertor (ADC), which can be optionally integrated with the device.

Although the examples provided in the present disclosure show a load cell, it is to be understood that any suitable force sensor may be employed for the measurement of the applied force. Non-limiting examples include force sensors based on piezoelectric transducers, strain gauge based devices, and devices involving spring movement.

Furthermore, although the aforementioned embodiments disclose a load cell that is integrated with third contact pad 150, it is to be understood that load cell 160 may be positioned externally to contact pad 150, and/or in any configuration that is suitable for measuring, whether directly or indirectly, the force applied by the subject under flexion or extension.

In the example embodiment shown in FIG. 1, first, second and third contact pads 130, 132 and 150 are shown as cylindrical in shape, having an annular form core surrounding a tubular cross member and an optional outer covering (not shown). Suitable example materials for the form core include medium density to firm density foam. In some embodiments, the contact pads may be closed-cell/coated, or open cell and covered with a washable cover such as vinyl. Other suitable examples of contact pads include those conventionally employed in or on fitness equipment. The thickness of the contact pads may be selected such that the wearer may produce a maximum amount of flexion or extension without substantial pain or discomfort. For example, in embodiments involving a cylindrical foam core with a medium to firm density, the radial thickness of the foam core may be approximately 1" (with a hollow core of approximately 1") for the arm pads, and 1.5"-1.25" for the leg pads. The contact pads may be concave in shape. It is to be understood that a suitable radial thickness of the foam core may depend on the density of the cushioning material. Furthermore, it is to be understood that other padding configurations, other than cylindrical contact pads, may be employed without departing from the scope of the present disclosure. For example, in other example embodiments, the contact pads may be contoured and/or pivoting.

Although limb strength measurement device 100 is shown in a configuration for measuring isometric flexion force, the device may be reconfigured for the measurement of isometric extension force, as further described below. In some embodiments, the device may be reconfigured between flexion and extension configurations without the need to remove the device from the limb.

Figure 2B:
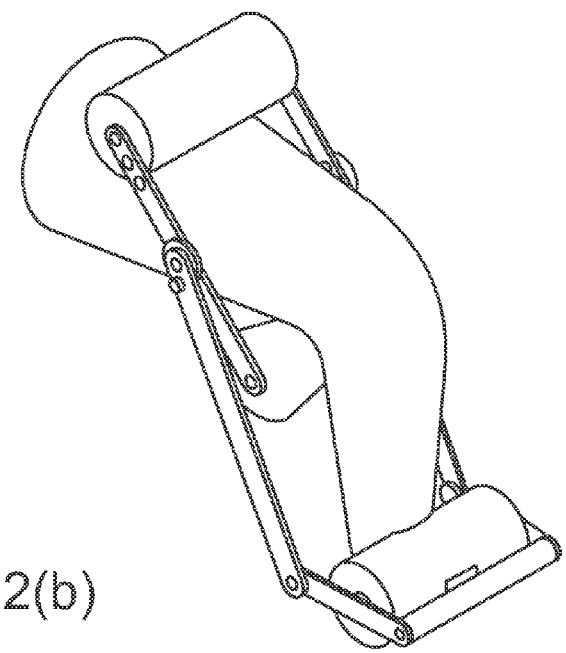

According to one embodiment, the limb strength measurement device may be provided in two sizes: a smaller size suitable for the arm, and a larger size for the leg. FIG. 2 illustrates embodiments in which the isometric limb strength measurement device is sized for (a) an arm (mounted for measurement of isometric flexion force) and (b) a leg (mounted for measurement of isometric extension force).

Although the device is shown in the present examples as being suitable for use in measurement of leg or arm strength, it is to be understood that in other embodiments, the device may be sized for the measurement of other limbs or bodily appendages, members, or extensions that include a joint, such as, but not limited to, those such as wrist and ankle, for which joint flexion/extension forces are measurable.

Figure 3:
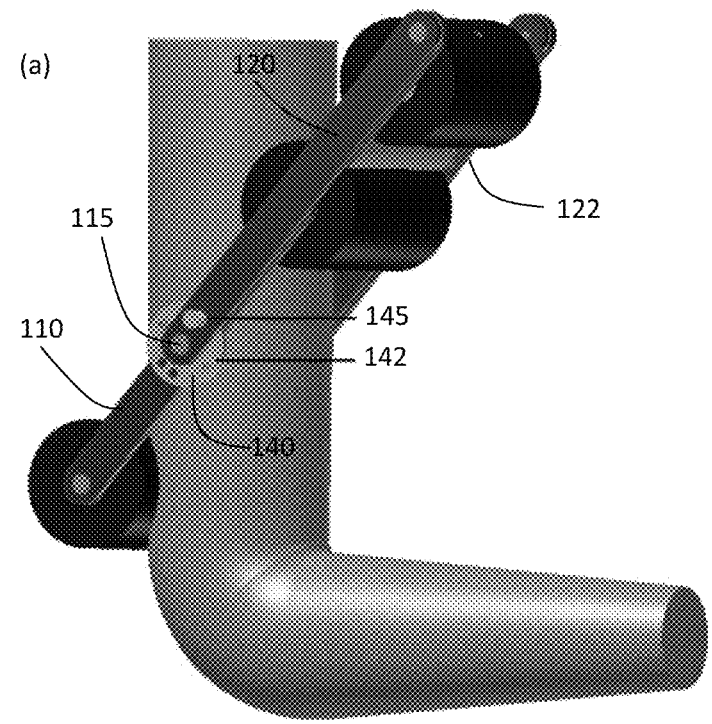
FIGS. 3 (a) and (b) illustrate an example method of configuring the limb strength measurement device for the measurement of isometric flexion force.
Figure 3:
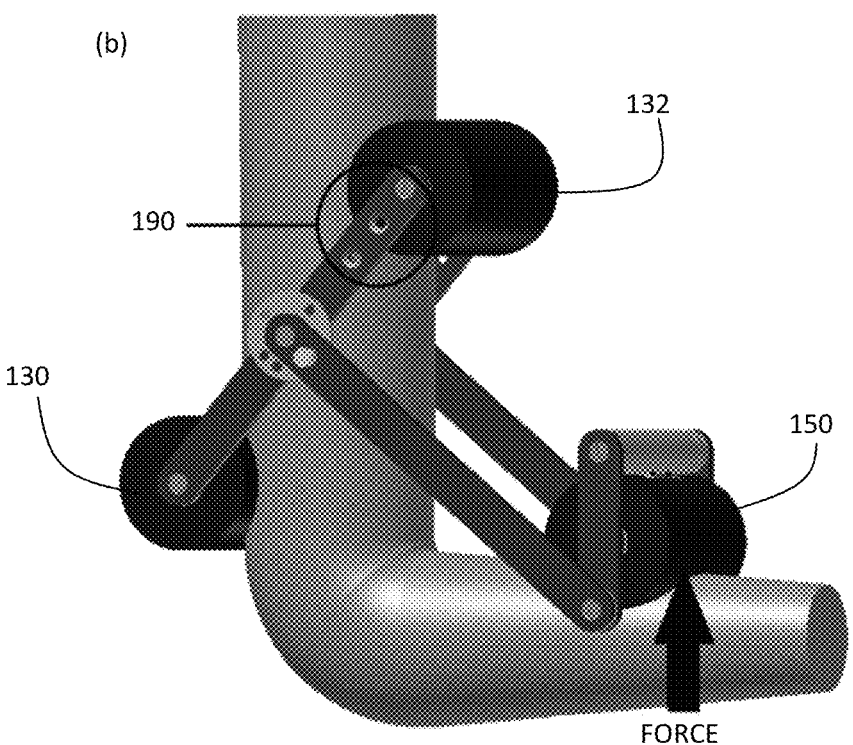
Figure 4:
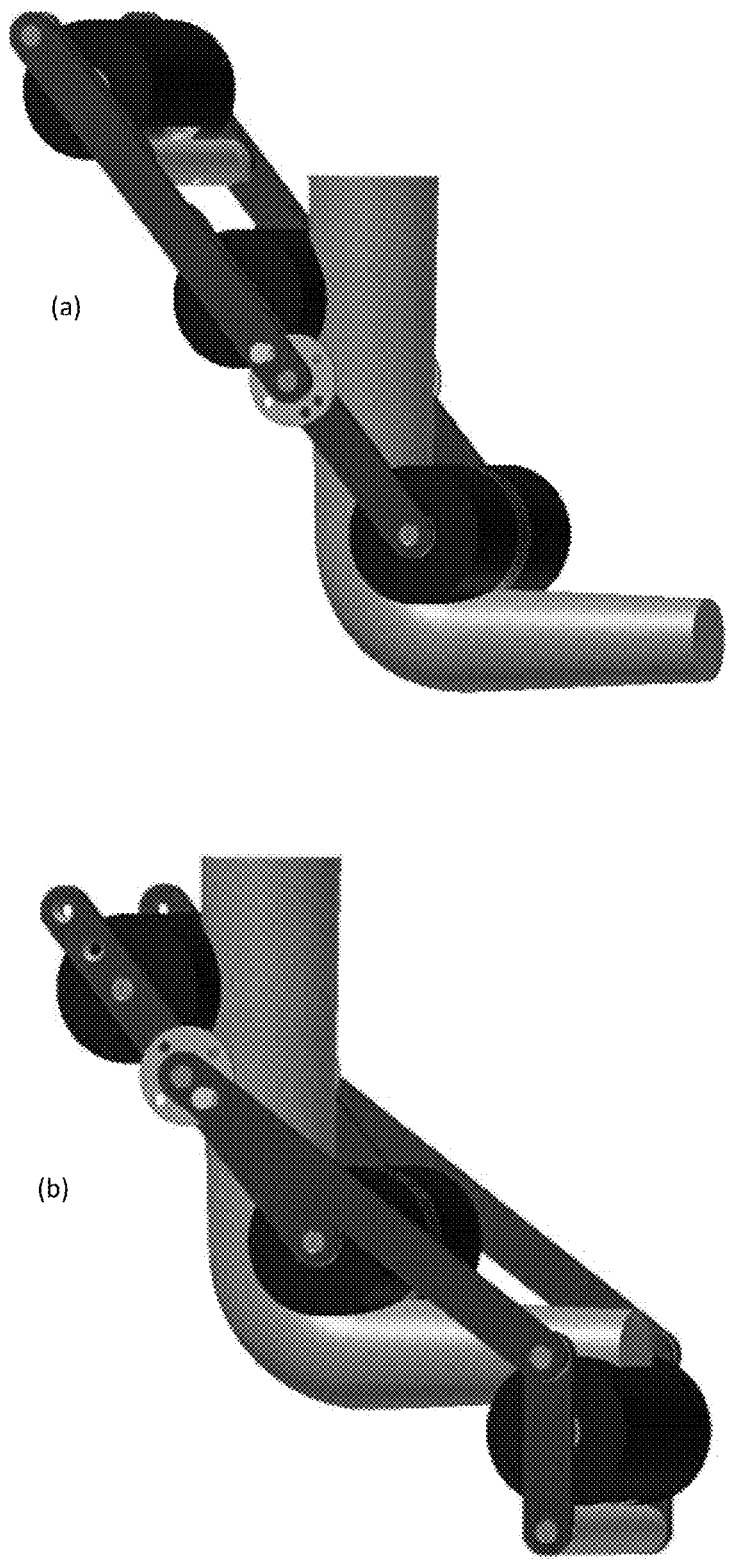
FIGS. 4 (a) and (b) illustrate an example method for reconfiguring the isometric limb strength measurement device for the measurement of isometric extension force, without needing to remove the device from the subject.

FIGS. 3 and 4 provide example embodiments illustrating methods and configurations for mounting the isometric limb strength measurement device. As described below, embodiments of the isometric limb strength measurement device enable the measurement of flexion and/or extension.

FIG. 3(*a*) illustrates an optional compact configuration for mounting the device on a subject. In this configuration, second pair of longitudinal members 120, 122 are rotated relative to pivot point 115 so that their longitudinal axis is parallel to the longitudinal axis of first pair of longitudinal members 110, 112. For each side of the device, locking pin 145 is inserted into a hole in locking plate 140 in order to maintain this alignment. The subject's arm may then be inserted in the gap between first pair of longitudinal members 110, 112, as shown in the Figure. This configuration, given its compact and uniaxial configuration, is also suitable for storing the device when not in use.

After having inserted the subject's arm, locking pin 145 is removed on each side, and second pair of longitudinal arms 120, 122 are rotated such that first, second and third contact pads 130, 132 and 150 contact the arm as shown in FIG. 3(*b*). Locking pin 145 is then engaged into the appropriate "flexion" hole in locking plate 140 to lock the device in place with the subject's arm at a suitable angle (such as an angle of approximately 90 degrees or 60 degrees). A plurality of locking holes may be provided to enable locking of the device in a number of different angles. For example, holes may be provided to lock the device in a series of angles differing by a fixed increment.

Once positioned and locked, the isometric limb strength device may be employed for measuring limb strength under the application of a flexion force. The subject applies a flexion force against third contact pad 150 with his/her forearm. Load cell 160 located in the third contact pad 150 measures the applied force.

FIGS. 4(*a*) and (*b*) illustrate the reconfiguration of the isometric limb strength measurement device for the measurement of an extension force. As shown in the Figure, changing from a flexion configuration to an extension configuration may be performed without the need to remove the device from the limb. The device may be first repositioned, from its configuration in FIG. 3(*b*), into its compact form as shown in FIG. 3(*a*). The device may then be rotated 180 degrees about the limb, such that the device is repositioned as shown in FIG. 4(*a*).

Locking pin 145 is then removed on each side, and second pair of longitudinal arms 120, 122 are rotated such that first, second and third contact pads 130, 132 and 150 contact the arm as shown in FIG. 4(*b*). Locking pin 145 is then engaged into the appropriate "extension" hole in locking plate 140 to lock the device in place with the subject's arm at a suitable angle (again, such as an angle of approximately 90 degrees). Once positioned and locked, the isometric limb strength device may then be employed for measuring limb strength under the application of an extension force. The subject applies an extension force against third contact pad 150 with his/her forearm. Load cell 160 located in the third contact pad 150 measures the applied force.

As noted above, the relative locations of contact pads 120, 130 and 150, and the lockable angular orientation of first 110,122 and second 120, 122 longitudinal members allow the device to be self-stabilizing and self-aligning with the subject's anatomical features when the subject is exerting force on the device. Accordingly, the self-contained design provides the restraining force that opposes the subject's developed force, and thus does not require physical coupling, connection or restraining between the subject and the outside world through a floor, wall, chair or any other immovable objects.

For example, as shown in FIG. 3(*b*), when the subject tries to flex the arm by pressing the forearm against the contact pad near the wrist, the contact pad near the elbow presses into the back of the elbow and the contact pad near the shoulder presses into the front of the shoulder. Similarly, as shown in FIG. 4(*b*), when the subject tries to extend the arm by extending the forearm against the contact pad near the wrist, the contact pad near the shoulder presses into the back of the shoulder and the contact pad near the elbow presses into the front of the elbow.

Although the first and second pairs of longitudinal members are shown as single part members, it is to be understood that any member may be made up of more than one part or segment. In one example embodiment, second longitudinal members 120, 122 may each include a first segment and a second segment extendable to multiple lengths from the first segment, with a locking mechanism such as a locking pin for locking a given configuration (in other examples, an extendable member may be realized via telescoping tubular segments with a simple spring-loaded locking mechanism). Such an embodiment allows the overall length of each member 120 and 122 may be varied, which may be useful for accommodating different body sizes and types, ages, or limb types (e.g. arm vs. leg). Furthermore, it is to be understood that any longitudinal members of the device need not be straight in shape. For example, in some embodiments, one or more longitudinal members may be curved over at least a portion of their length. Moreover, a member could include a variety of curves and bends and folds of material that are suitable for comfort, fit, aesthetic look, and/or resistance to lateral and medial bends for multidimensional stiffness to resist twisting of the overall device.

In the aforementioned embodiments, the isometric limb strength measurement device involved the use of a locking mechanism to fix a suitable orientation of the device, and the use of a load cell to locally measure the force applied to a contact pad. In alternative embodiments, the first pair and second pair of longitudinal members may be pivotally connected and coupled to a force measurement device, such that the force applied to the third contact pad is measured indirectly, at a location remote from the point of application of the force, and where the force measurement device opposes or restricts pivotal motion of the first pair of longitudinal members relative to the second pair of longitudinal members beyond a pre-selected angle.

Figure 5A:
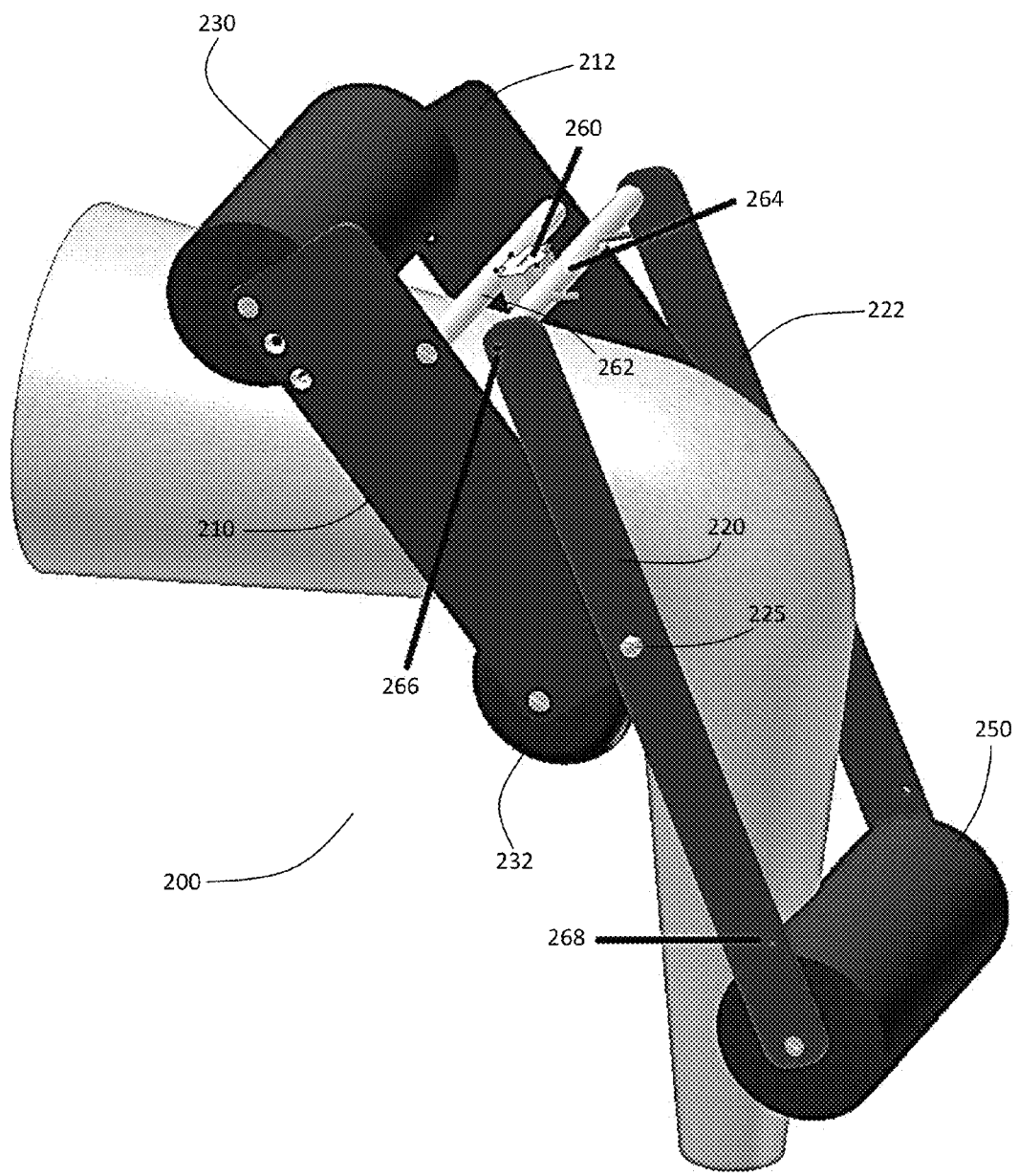
FIG. 5 illustrates an embodiment of an isometric limb strength measurement device configured for the indirect measurement of the flexion or extension force applied to the device by a knee joint, showing (a) the device positioned for measurement of the extension force, (b) the device in a collapsed state prior to being rotated into a flexion configuration, and (c) the device positioned for measurement of the flexion force.

One such embodiment is illustrated in FIG. 5(a). Isometric limb strength measurement device 200 includes first pair of longitudinal members 210, 212 and a second pair of longitudinal members 220, 222 that are pivotally attached at pivot point 225. As in the preceding embodiments, first and second contact pads 230 and 232 are supported near ends of first pair of longitudinal members 210, 212. Third contact pad 250 is supported near a distal end of second pair of longitudinal members 220, 222.

As shown in FIG. 5(a), in an embodiment, the load cell 260 is compressed when first and second pairs of longitudinal members pivot beyond a pre-selected angle, thereby allowing measurement of a force applied by the subject to third contact pad 250. The compression of load cell 260 occurs due to first and second connecting rods 262 and 264, where first connecting rod 262 is attached to first pair of longitudinal members 210, 212, and where second connecting rod 264 is attached to second pair of longitudinal members 220, 222.

Figure 5B:
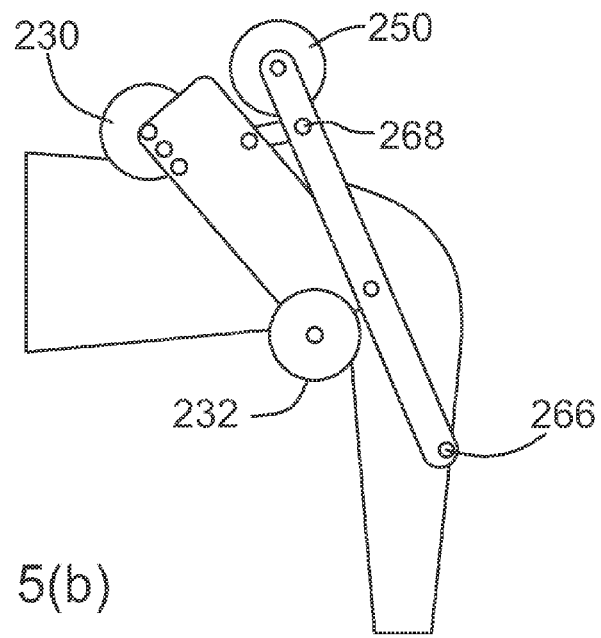
Figure 5C:
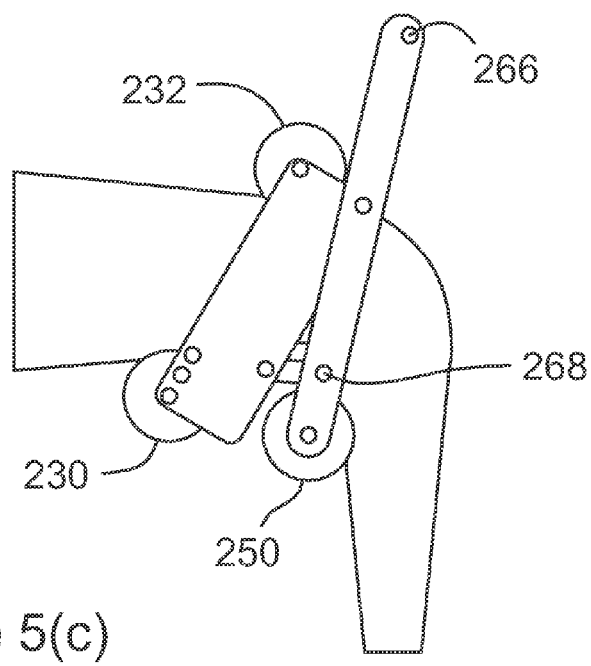

In the embodiment shown in FIG. 5(a), connecting rod 264 is equipped with spring-loaded pins which fit into two separated sets of holes 266 and 268 such that the device may be configured for either extension or flexion. As shown in the Figure, changing from an extension configuration to a flexion configuration may be performed without the need to remove the device from the limb. The device may be first repositioned, from its configuration in FIG. 5(a), into its compact form as shown in FIG. 5(b) by releasing the spring loaded pins in the connecting rod 264 from the hole 266 and then the pair of longitudinal arms 220, 222 are rotated such that hole 268 is aligned with connecting rod 264's spring loaded pins and locked. The device may then be rotated 180 degrees about the upper limb, such that the device is repositioned as shown in FIG. 5(c) with the contact pads 230, 232 and 250 contacting the subject's limb.

Figure 6A:
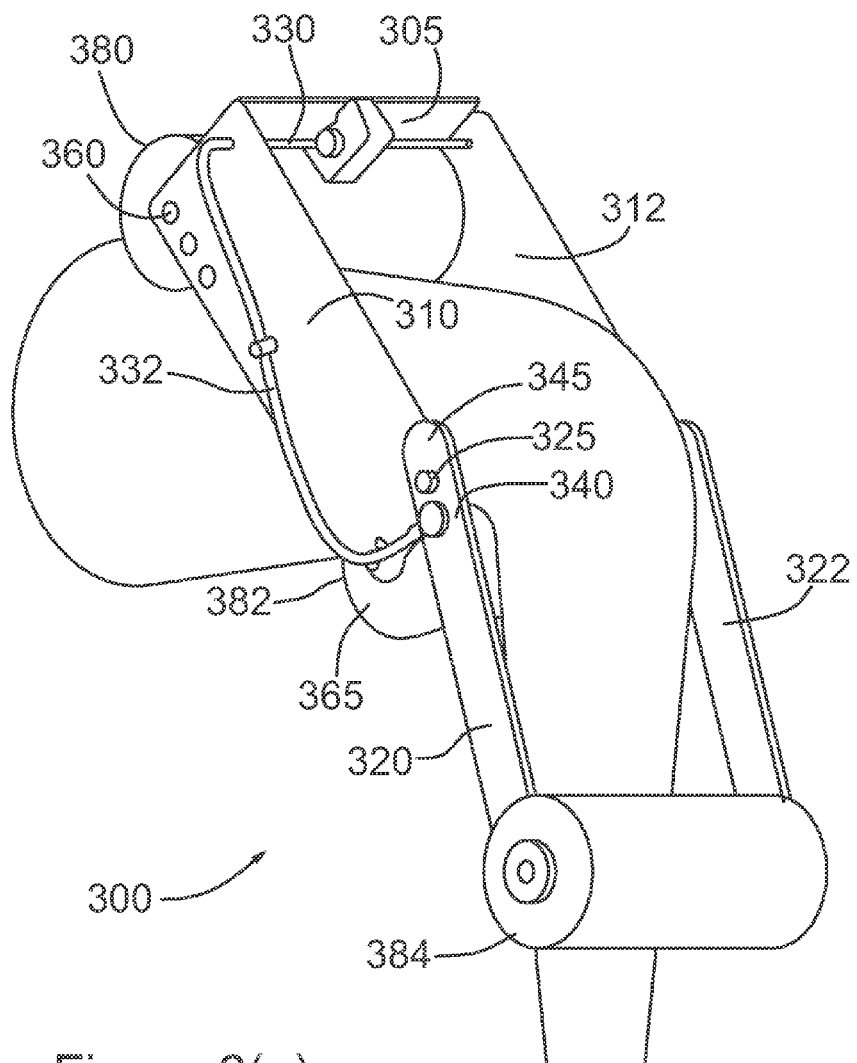
FIG. 6 illustrates another embodiment of an isometric limb strength measurement device configured for the indirect measurement of the flexion or extension force applied to the device by a knee joint, showing (a) the device positioned for measurement of the extension force, (b) the device in a collapsed state prior to being rotated into a flexion configuration, and (c) the device positioned for measurement of the flexion force.

FIG. 6(a) shows an alternative embodiment of device 300, in which the load cell 305 is held in a case mounted between first of longitudinal plates 310, 312. A cable 330 connects end of the load cell 305 and each bar of the distal linkage. In the reconfigurable embodiment shown, members 320 and 322 each include an attachment hole on either side of the pivot bolt 325. A hand-tightened knob-bolt 340 secures the cable end to the appropriate attachment hole 345 for either flexion or extension. Cable sheath 332 is firmly attached each of members 310 and 312, where attachment points for member 310 are shown in the Figure at locations 360 and 365.

Figure 6B:
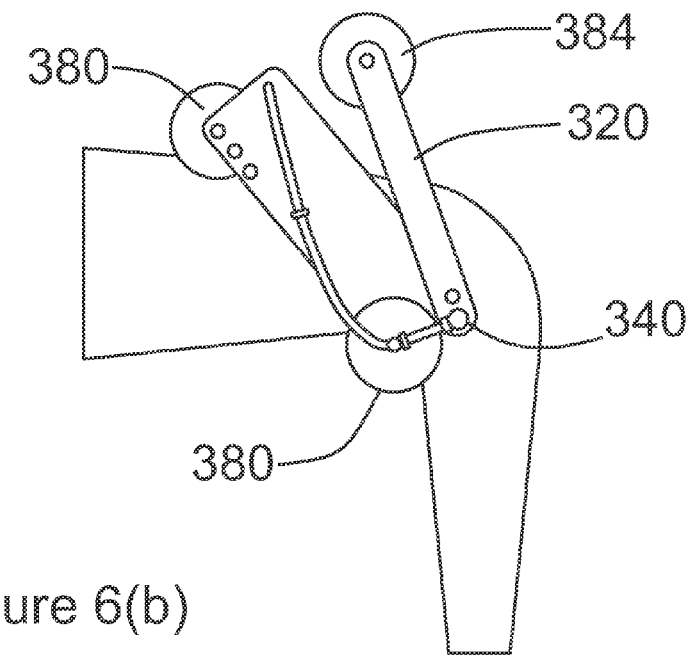
Figure 6C:
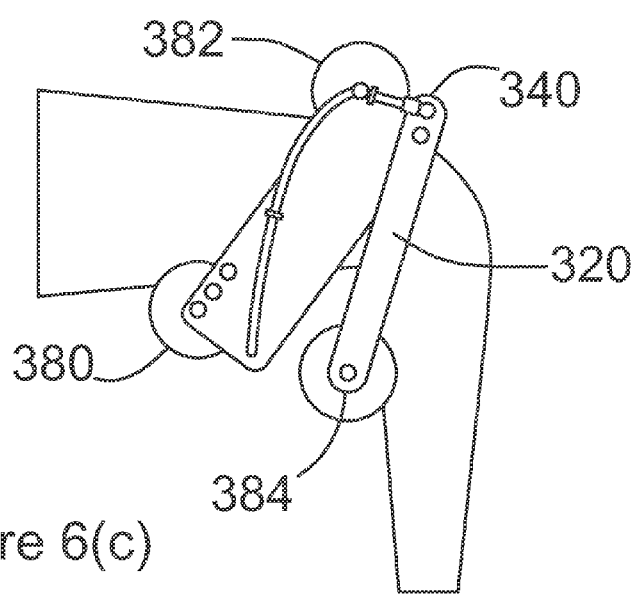

As shown in the Figure, changing from an extension configuration to a flexion configuration may be performed without the need to remove the device from the limb. The device may be first repositioned, from its configuration in FIG. 6(a), into its compact form as shown in FIG. 6(b) by removing the hand tightened knob-bolt 340 from the hole in the member 320 and then the pair of longitudinal arms 320, 322 are rotated such that hole 345 is aligned with knob-bolt 340 and hand tightened (in FIG. 6(b), hole 345 is covered by knob-bolt 340). The device may then be rotated 180 degrees about the upper limb, such that the device is repositioned as shown in FIG. 6(c), with the contact pads 380, 382 and 384 contacting the subject's limb.

Although the preceding embodiments of this disclosure describe double-sided devices including parallel members in a spaced relationship, it is to be understood that some embodiments may only involve unpaired members that reside on one side of a limb when the device is worn. For example, with reference to the embodiments shown in FIGS. 1-4, any one or more of members 112, 122, and 182 may be omitted, such that first and second contact pads 130, 132 extend laterally from first member 110, and third contact pad 150 extends laterally from second member 120.

Figure 7:
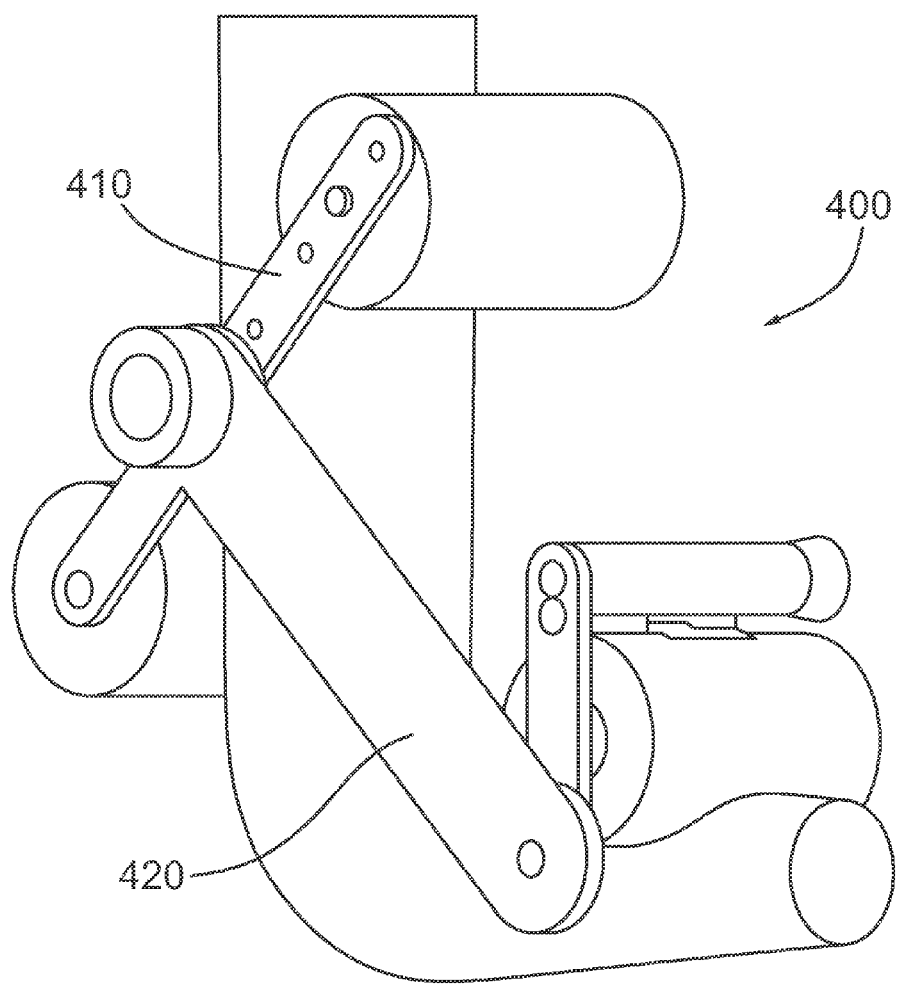
FIG. 7 illustrates a single-sided example embodiment of a limb strength measurement device, shown in a configuration for measuring arm strength.

FIG. 7 shows a single-sided embodiment 400 of the arm limb strength measurement device. In comparison with FIG. 1, members 112, 122 and 182 have been removed. Member 420 is increased in width (shown by the white arrow as doubling in width relative to the embodiment of FIG. 1, for example, from one to two inches) to increase its stiffness and resist twist. Donning the device is easier than the double-sided version.

In one embodiment, the device may be configured as follows for performing an arm strength measurement. Device 400 is locked into position for either flexion or extension. It is then slid, from the side, over the arm which is waiting with the appropriate amount of flexion. (It is also possible to provide a device for leg strength measurement, however a sufficient amount of reinforcement of the members would be needed to prevent twisting).

The following examples are presented to enable those skilled in the art to understand and to practice the present invention. They should not be considered as a limitation on the scope of the invention, but merely as being illustrative and representative thereof.

EXAMPLES

The purpose of this example study was to evaluate the performance of an example implementation of the aforementioned device as a measurement tool to assess knee extension maximal voluntary isometric contraction (KE-MVIC) in young healthy adults. As described below, and as shown in FIG. 8(c), the embodiment of the present disclosure that was employed during testing, henceforth referred to as the LSMD, corresponded to the example embodiment shown in FIG. 2(b).

Methods and Materials

Ten adults (5 females) between the ages of 21 to 43 years were recruited through the local university community. All participants were screened prior to enrollment and were excluded if they had any musculoskeletal or neurological condition affecting the lower extremities or any contraindications to moderate exercise.

Figure 8A:
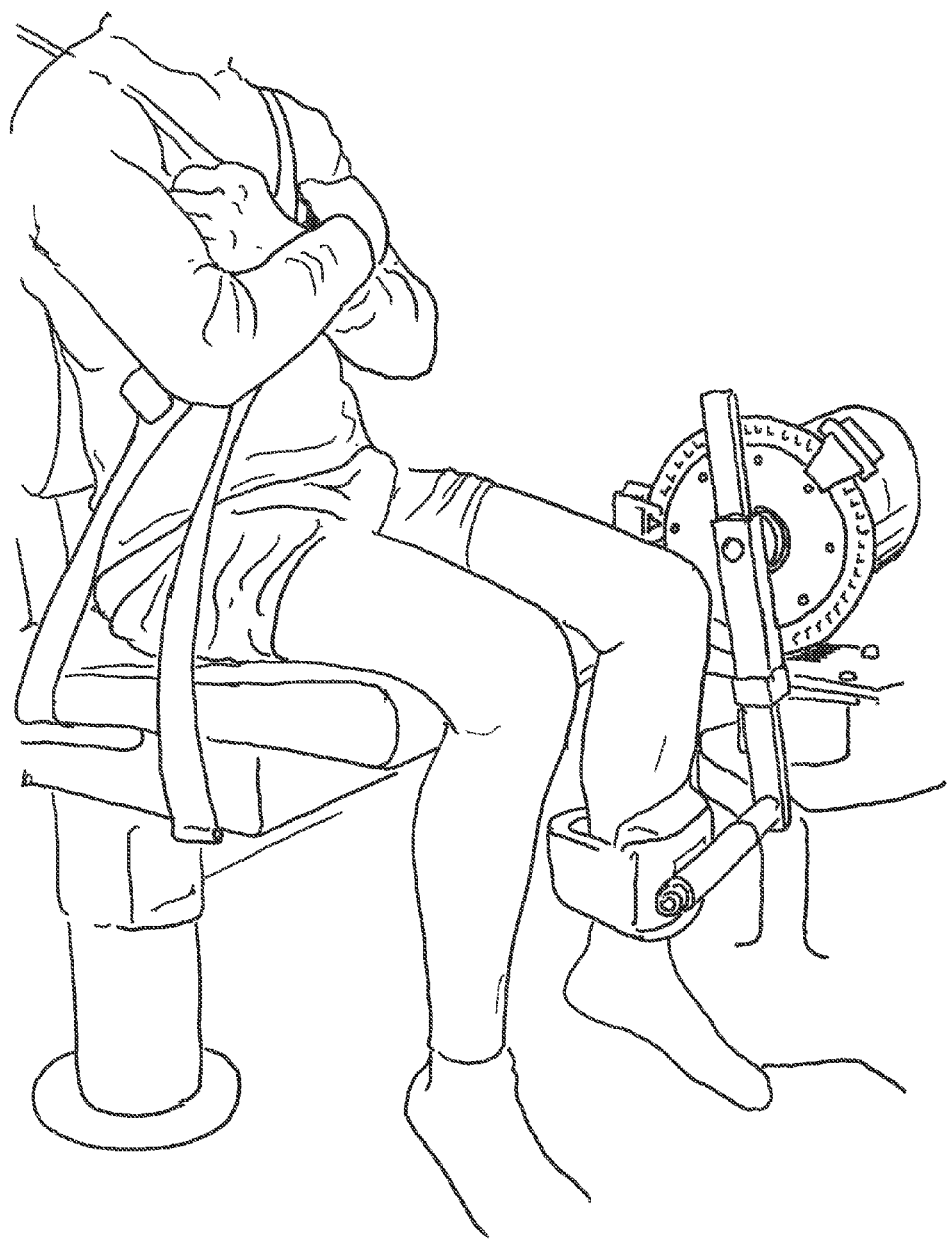
FIG. 8 shows photographs of known devices employed in the example study, where (a) shows an isokinetic dynamometry (IKD) device, (b) shows a handheld device as used in a testing position, and (c) shows an embodiment of the limb strength measurement device employed during testing.
Figure 8B:
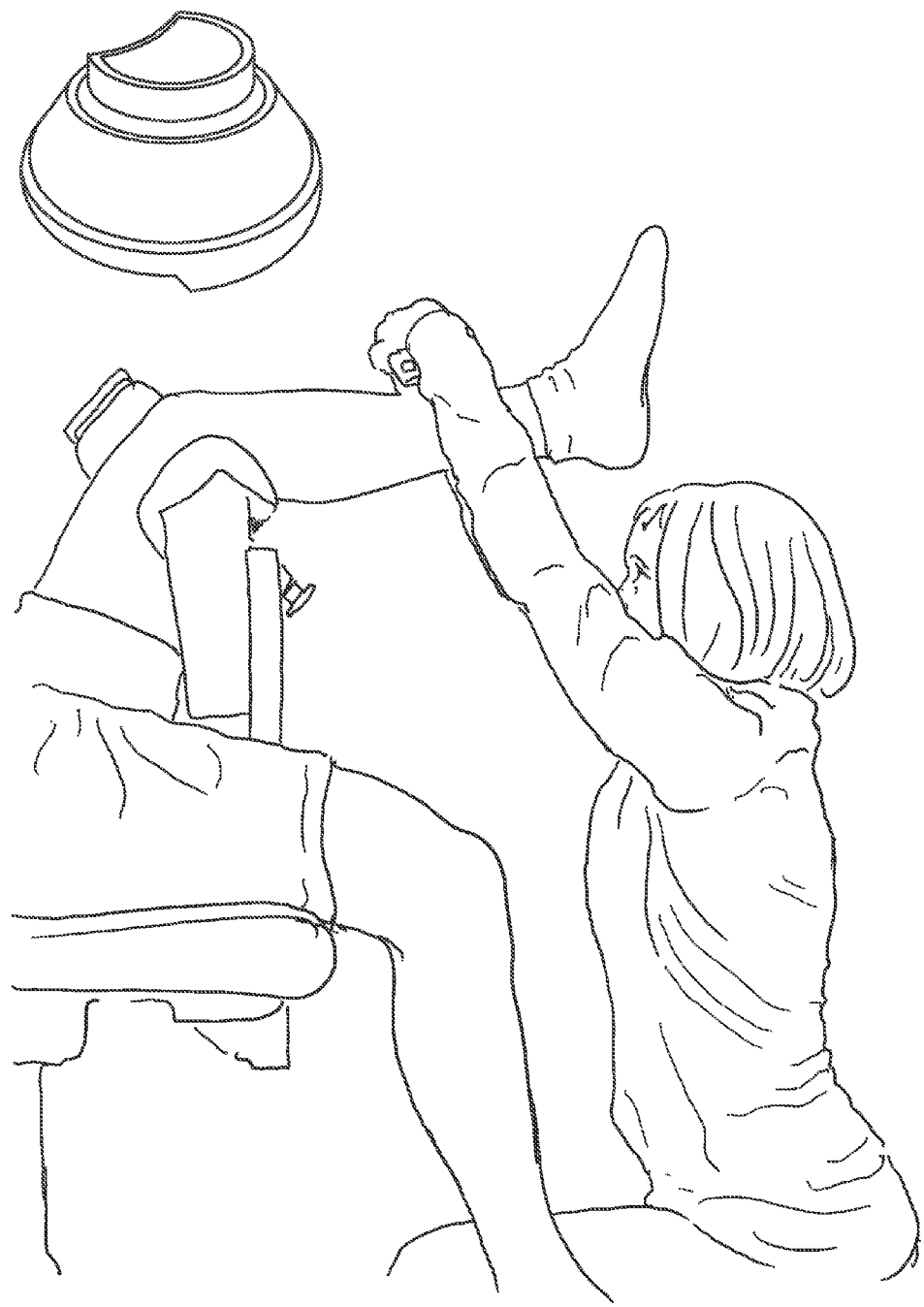
Figure 8C:

Participants were tested for both right and left KE-MVIC using three independent devices: the Cybex Humac Norm™ isokinetic dynamometer (IKD, FIG. 8(a)), the Microfet2™ handheld dynamometer (HHD, FIG. 8(b)), and the limb strength measurement device (LSMD) shown in FIG. 8(c)). Testing order of devices and legs was determined by a randomly generated table. Three MVIC repetitions were collected, with a 60 second rest between repetitions, and approximately 3-5 minutes between device tests.

Testing protocols for IKD and HHD were similar to published reports for assessing KE-MVIC. One exception was that the HHD used a modified protocol to enable stable tester posture (see FIG. 8(b)). The protocol for LSMD testing followed the methods described in the above disclosure. The external knee moment arm was the same for all three devices.

For all devices, legs and repetitions tested, the peak force measured (lbs force) during the trial was recorded. These data were reduced to device x legs using the maximum of the three repetitions to present the MVIC achieved for a particular device.

The following hypotheses were tested using SPSS (v20, IBM Corp):
1) Paired t-tests between IKD-LSMD, IKD-HDD and LSMD-HDD required that the null hypothesis be rejected for IKD-HDD and LSMD-HDD comparisons (they are different), and accepted for IKD-LSMD comparison (they are similar);
2) When regressing LSMD with IKD, and HDD with IKD, the LSMD will explain more variance in IKD measurement than HDD can explain; and
3) Inter-subject variability (based on repetition trials) of the LSMD should be on par with that of the gold-standard IKD.

Study Results

The primary working hypothesis was supported. The LSDM and IKD were significantly different from HDD ($p<0.001$), while LSMD and IKD were not different from one another ($p=0.44$). This suggests that on average, the LSMD was capable of measuring KE-MVIC more faithfully than the HHD was capable of. Although it was not statistically significant, it is still worth noting that the LSMD slightly underpredicted the KE-MVIC, when compared to the gold-standard IKD measurement.

Figure 9:
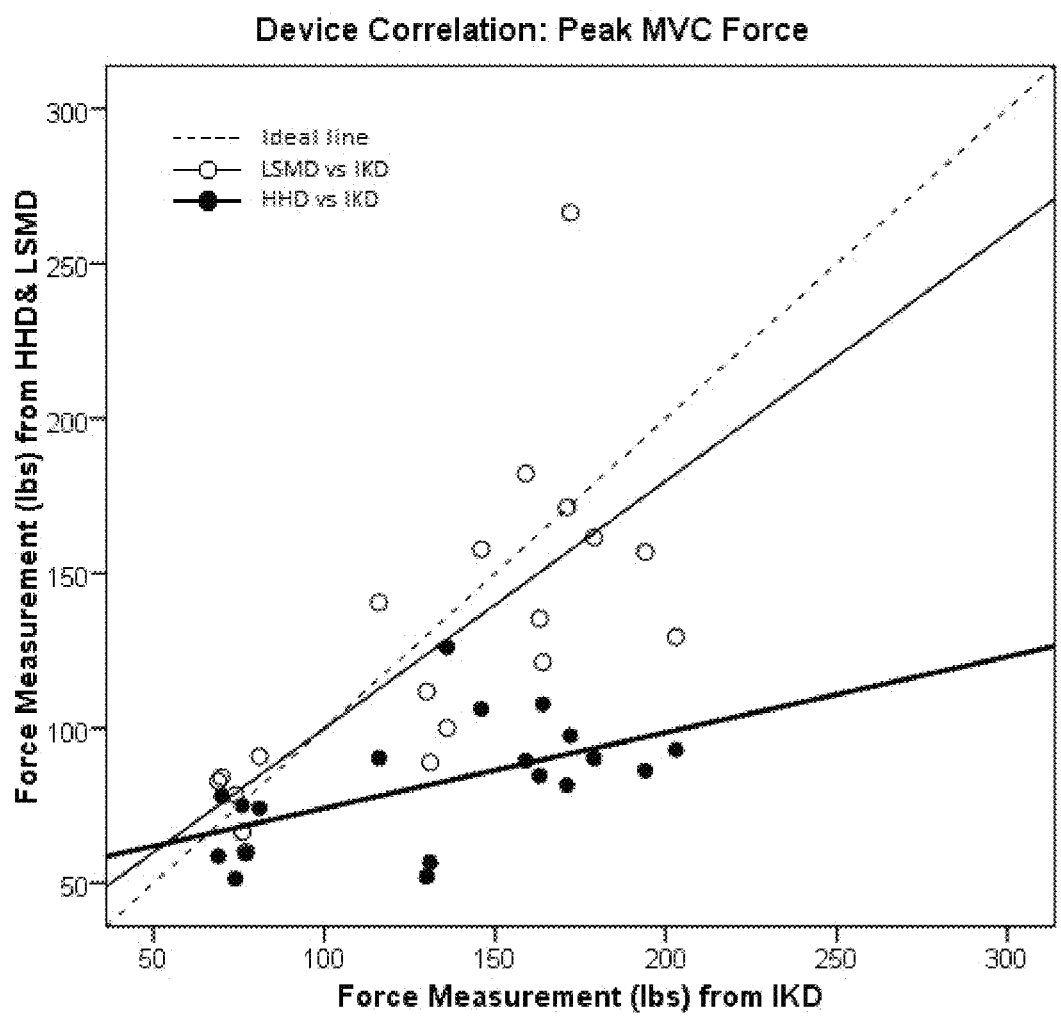
FIG. 9 plots regression lines for the handheld device and the present device versus the IKD device. The dashed line represents a perfect 1:1 correspondence.

The secondary working hypothesis was also supported. FIG. 9 shows that the LSMD explained more than 54% of the variance in IKD measurement, while the HHD explained less than 33% of the variance in IKD measurement.

Figure 10:
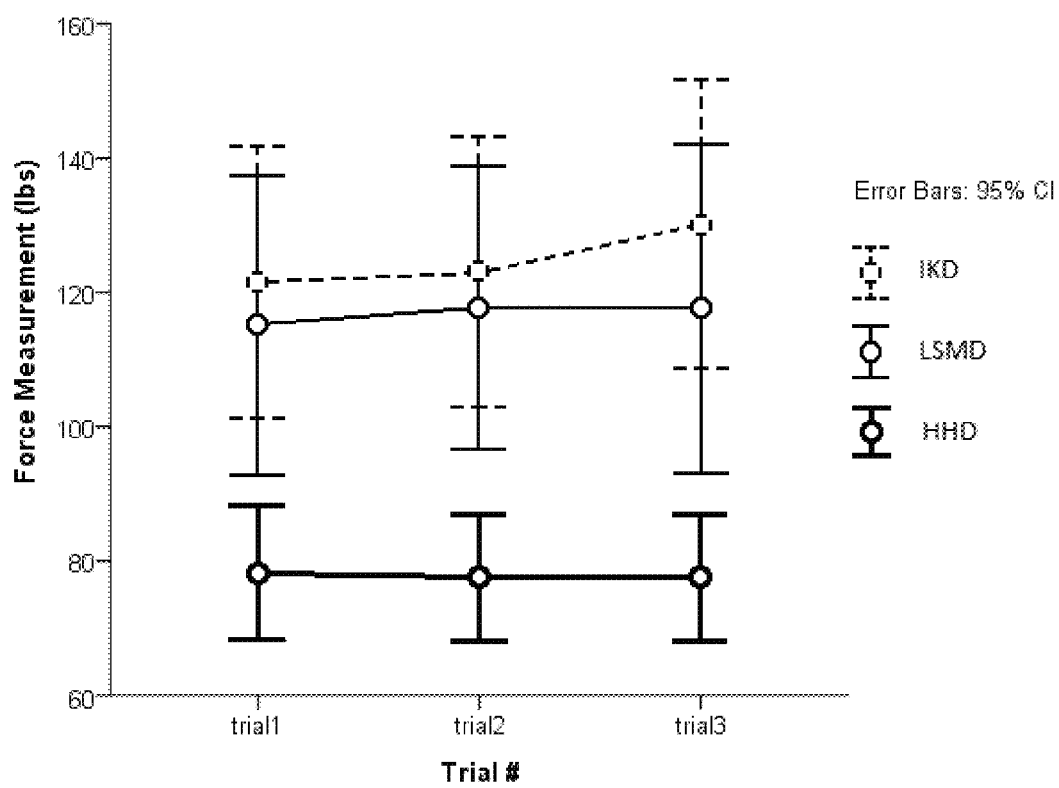
FIG. 10 plots results from ordered trials for each of the three devices used in the example study.

FIG. 10 provides further insight into the variance among devices, showing the variance across the ordered trials for each of the three devices. The IKD and LSMD did in fact show very similar variability across trials, but both were considerably higher than the variability in HDD measurement. This indicates that IKD and LSMD are heteroscedastistic, which means that variability in KE-MVIC increases with increasing strength, and therefore more than three repetitions may be required in future studies, as suggested previously.

Although IKD systems are often available in research labs and rehab hospitals in large urban centers, they are generally inaccessible to the clinical and athletic training professions. HHD technology offers a simple solution for wide accessibility, but is not always reliable for measuring MVIC in major muscle groups such as the knee quadriceps.

It is noted that although the present study only recruited healthy young adults, it was necessary to do so for preliminary testing of such a device, given that not all populations with knee joint disease or injury have compromised strength, which requires a robust device capable of measuring joint force linearly from the weakest to the strongest of individuals.

This example study suggests that the LSMD can provide a valid and accessible technology for clinical and field work where knee joint MVIC is required, with results of similar accuracy to the gold standard IKD measurements. It is further noted that the LSMD, and other related embodiments (as described above) may also be beneficial in a wide range of clinical and research applications. For example, the LSMD may be beneficial in populations with neurologic injury (stroke, cerebral palsy, multiple sclerosis and spinal cord injury) where HHD measurement of strength may be more reflective of muscle rigidity than contractile strength, and hence a truly objective way to assess voluntary muscle strength is needed, without requiring access to an IKD system.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Therefore what is claimed is:

1. A limb strength measurement device for measuring strength of a limb under isometric flexion or extension, the limb having a first portion and a second portion pivotable about a joint, the device comprising:
   a first pair of longitudinal members provided in a spaced relationship, wherein a gap between said first pair of longitudinal members is suitable for insertion of the limb therethrough,
   a first contact pad supported between said first pair of longitudinal members near a first end thereof;
   a second contact pad supported between said first pair of longitudinal members near a second end thereof;
   a second pair of longitudinal members provided in a spaced relationship, wherein said second pair of longitudinal members are pivotally connected to said first pair of longitudinal members near a first end of said second pair of longitudinal members, and wherein a gap between said second pair of longitudinal members is suitable for insertion of the limb therethrough;
   a third contact pad coupled to said second pair of longitudinal members near a second end thereof,
   a locking mechanism for locking an angular orientation of said second pair of longitudinal members relative to said first pair of longitudinal members, such that when said device is worn, said first contact pad and said second contact pad contact opposing sides of the first portion of the limb, and said third contact pad contacts the second portion of the limb, thereby securing said device relative to the limb; and
   a force measurement device configured to measure a force applied to said third contact pad by the second portion of the limb.

2. The device according to claim 1 wherein said device is reconfigurable for the measurement of an isometric extension force or and isometric flexion force.

3. The device according to claim 2 wherein said device is reconfigurable while being worn by a subject.

4. The device according to claim 1 wherein a length of said second pair of longitudinal members is sufficient to allow said second pair of longitudinal members to be pivoted such that they are aligned with said first pair of longitudinal members.

5. The device according to claim 4 wherein said locking mechanism includes a feature for locking said device when said second pair of longitudinal members are aligned with said first pair of longitudinal members.

6. The device according to claim 1 wherein each of said first contact pad and said second contact pad includes:
   a cross member connecting said first pair of longitudinal members;
   a cylindrical padded portion surrounding said cross member.

7. The device according to claim 6 wherein said cylindrical padded portion is formed from a compressible foam material.

8. The device according to claim 7 wherein said cylindrical padded portion has a radial thickness between approximately 1 and 1.5 inches.

9. The device according to claim 6 wherein said cylindrical padded portion has a radial thickness sufficient to prevent substantial discomfort during application of maximum force by a subject wearing said device.

10. The device according to claim 1 wherein a relative distance between said first contact pad and said second contact pad is variable.

11. The device according to claim 10 wherein said first pair of longitudinal members include connection holes for positioning said first contact pad or said second contact pad in two or more locations along a longitudinal extend of said first pair of longitudinal members.

12. The device according to claim 1 wherein said locking mechanism includes:
   a locking plate secured to a first member of said first pair of longitudinal members and/or said second pair of longitudinal members, the locking plate including one or more locking holes; and
   a locking pin provided in a second member of said first pair of longitudinal members and/or said second pair of longitudinal members, wherein said second member is pivotally attached to said first member;
   wherein said locking pin is receivable within said locking hole for locking said second member to said first member.

13. The device according to claim 12 wherein one or more of said locking holes is positioned for locking said device in a plurality of angles.

14. The device according to claim 1 wherein said force measurement device is configured for local measurement of the force applied to said third contact pad.

15. The device according to claim 1 to wherein said force measurement device is a load cell.

16. The device according to claim 15 wherein said load cell is connected on a first side thereof to said third contact pad, and wherein said load cell is connected on a second side thereof to a connecting member, and wherein said connecting member is coupled to said second pair of longitudinal members, such the force applied to said third contact pad is transmitted to said load cell.

17. The device according to claim 16 wherein said third contact pad includes:
   a central member;
   a cylindrical padded portion surrounding said central member;
   wherein said load cell is connected to said central member through a gap in said cylindrical padded portion.

18. The device according to claim 17 wherein said load cell is recessed within said third contact pad.

19. The device according to claim 16 wherein said connecting member is pivotally connected to said second pair of longitudinal members near said second end thereof.

20. The device according to claim 16 further comprising a third pair of members provided in a spaced relationship, wherein said second pair of longitudinal members are pivotally connected to said third pair of members near one end thereof, and wherein said connecting member is supported between said third pair of members near a second end thereof.

21. The device according to claim 20 further wherein said third pair of members are connected to said connecting member such that a longitudinal axis of said third pair of members is substantially parallel to an axis of said load cell under application of the force.

22. A limb strength measurement device for measuring strength of a limb under flexion or extension, the limb having a first portion and a second portion pivotable about a joint, the device comprising:
   a first longitudinal member;
   a second longitudinal member pivotally connected to said first longitudinal member near a first end of said second longitudinal member;
   a first contact pad extending laterally from said first longitudinal member near a first end thereof;
   a second contact pad extending laterally from said first longitudinal member near a second end thereof;
   a third contact pad coupled to said second longitudinal member near a second end thereof,
   a locking mechanism for locking an angular orientation of said second longitudinal member relative to said first longitudinal member, such that when said device is worn, said first contact pad and said second contact pad contact opposing sides of the first portion of the limb, and said third contact pad contacts the second portion of the limb, thereby securing said device relative to the limb; and
   a force measurement device configured to measure a force applied to said third contact pad by the second portion of the limb.

23. A limb strength measurement device for measuring strength of a limb under isometric flexion or extension, the limb having a first portion and a second portion pivotable about a joint, the device comprising:
   a first pair of longitudinal members provided in a spaced relationship, wherein a gap between said first pair of longitudinal members is suitable for insertion of the limb therethrough,
   a first contact pad supported between said first pair of longitudinal members near a first end thereof;
   a second contact pad supported between said first pair of longitudinal members near a second end thereof;
   a second pair of longitudinal members provided in a spaced relationship, wherein said second pair of longitudinal members are pivotally connected to said first pair of longitudinal members at a pivot location, and wherein a gap between said second pair of longitudinal members is suitable for insertion of the limb therethrough;
   a third contact pad supported between said second pair of longitudinal members near a first end thereof, wherein said first end of said second pair of longitudinal members is distal from said pivot location, and
   a force measurement device restricting pivotal motion of said second pair of longitudinal members beyond a preselected angle when said first contact pad and said second contact pad contact opposing sides of the first portion of the limb and third contact pad contacts the second portion of the limb;
   wherein said force measurement device is configured to indirectly measure a force applied to said third contact pad by the second portion of the limb.

24. The device according to claim 23 wherein said force measurement device includes a first cross member connecting said first pair of longitudinal members, a second cross member connecting said second pair of longitudinal members, and a load cell connected to one of said first cross member and said second cross member, wherein said first cross member and said second cross member are positioned such that the application of force to said third contact pad causes said load cell to be compressed between said first cross member and said second cross member.

25. The device according to claim 23 wherein said force measurement device includes a load cell, wherein said load cell is supported between said first pair of longitudinal members by a first cable attached to a first side thereof and a second cable attached to a second side thereof, wherein said first cable and said second cable are supported within a first sheath and a second sheath, respectively, wherein said first sheath is connected to a first member of said first pair of longitudinal members, and wherein said second sheath is connected to a second member of said first pair of longitudinal members, wherein said first cable is connected at a distal end thereof to a first member of said second pair of longitudinal members, and wherein said second cable is connected at a distal end thereof to a second member of said second pair of longitudinal members, such that a force applied to said third contact pad results in the application of tension to said load cell by said first cable and said second cable.

\* \* \* \* \*